United States Patent [19]

Ingolia et al.

[11] Patent Number: 4,950,603
[45] Date of Patent: Aug. 21, 1990

[54] **RECOMBINANT DNA EXPRESSION VECTORS AND DNA COMPOUNDS THAT ENCODE ISOPENICILLIN N SYNTHETASE FROM *STREPTOMYCES LIPMANII***

[75] Inventors: Thomas D. Ingolia; Barbara J. Weigel, both of Indianapolis, Ind.

[73] Assignee: Eli Lilly and Company, Indianapolis, Ind.

[21] Appl. No.: 115,950

[22] Filed: Nov. 2, 1987

[51] Int. Cl.$^5$ .................... C12N 7/00; C12N 15/00; C12N 1/20; C07H 15/12

[52] U.S. Cl. .................... 435/235; 435/172.3; 435/183; 435/252.33; 435/252.35; 435/320; 536/27; 935/14; 935/29; 935/31; 935/48; 935/73; 935/75

[58] Field of Search .................... 435/183, 172.3, 235, 435/252.3, 252.33, 252.35, 320; 536/27; 935/14, 29, 73, 75

[56] References Cited

U.S. PATENT DOCUMENTS

| | | | |
|---|---|---|---|
| 4,885,251 | 12/1989 | Ingolia et al. | 435/183 |
| 4,885,252 | 12/1989 | Ingolia et al. | 435/252.3 |
| 4,892,819 | 1/1990 | Carr et al. | 435/69.1 |

OTHER PUBLICATIONS

Jenson et al. Manuscript Made Available to Applicant, Oct. 1987.
Ramon et al. *Gene* 57:171-181, 1987.
Adelman et al., *DNA* 2:183-193 (1983).
Maniatis et al., *Molecular Cloning* 140 (1982).
Ingolia and Queener, *Med. Res. Rev.* 9:245-264 (1989).

*Primary Examiner*—Thomas D. Mays
*Attorney, Agent, or Firm*—Amy E. Hamilton; Leroy Whitaker

[57] ABSTRACT

DNA compounds encoding the *Streptomyces lipmanii* isopenicillin N synthetase (IPNS) gene are useful for constructing a variety of recombinant DNA vectors. The vectors are useful in producing IPNS in a wide variety of host cells, such as Streptomyces, Penicillium, and Cephalosporium. DNA compounds encoding the transcription and translation activating sequence and transcription termination sequence of the *S. lipmanii* IPNS gene are also useful in the construction of expression vectors, especially Streptomyces expression vectors. The *S. lipmanii* IPNS gene can be isolated from plasmid pOGO239, available from the Northern Regional Research Center under accession number NRRL B-18250.

23 Claims, 4 Drawing Sheets

Restriction Site and Function Map of Plasmid pOGO239 (5,500 bp)

Restriction Site and Function Map of Plasmid pOGO239
(5,500 bp)

Restriction Site and Function Map of Plasmid pOGO246
(5,500 bp)

Restriction Site and Function Map of Plasmid pCZR111
(6,395 bp)

Restriction Site and Function Map of Plasmid pOGO249
(7,186 bp)

RECOMBINANT DNA EXPRESSION VECTORS AND DNA COMPOUNDS THAT ENCODE ISOPENICILLIN N SYNTHETASE FROM *STREPTOMYCES LIPMANII*

The present invention comprises a DNA sequence that encodes the isopenicillin N synthetase activity of *Streptomyces lipmanii*. Isopenicillin N synthetase catalyzes the reaction in which isopenicillin N is formed from δ-(L-α-aminoadipyl)-L-cysteinyl-D-valine. This reaction is a critical step in the biosynthesis of important antibiotics such as penicillins from *Streptomyces lipmanii, Aspergillus nidulans, Penicillium chrysogenum, Cephalosporium acremonium*, and *S. clavuligerus;* cephalosporins from *C. acremonium;* and 7α-methoxy-cephalosporins from *S. clavuligerus* and *S. lipmanii.*

The novel DNA sequence that encodes the isopenicillin N synthetase activity was isolated from *Streptomyces lipmanii* and is useful to construct recombinant DNA expression vectors that drive expression of the activity. The present invention includes vectors that drive high-level expression of the isopenicillin N synthetase activity in many diverse host cells, such as Streptomyces, *E. coli*, Cephalosporium, Aspergillus, and Penicillium.

The *E. coli*-produced isopenicillin N synthetase activity catalyses the reaction that forms isopenicillin N from δ-(L-α-aminoadipyl-L-cysteinyl-D-valine. Crude cell extracts from *E. coli* host cells transformed with the *E. coli* vectors of the present invention exhibit isopenicillin N synthetase activity. The *E. coli* vectors of the present invention thus provide an efficient means for obtaining large amounts of active isopenicillin N synthetase. Isopenicillin N synthetase is useful, not only for the production of isopenicillin N, but also for the condensation of tripeptides other than δ-(L-α-aminoadipyl)-L-cysteinyl-D-valine to form novel antibiotics.

The DNA compounds encoding isopenicillin N synthetase are readily modified to construct expression vectors that increase the efficiency and yield of antibiotic fermentations involving organisms such as *Aspergillus nidulans, Cephalosporium acremonium, Penicillium chrysogenum, Streptomyces clavuligerus,* and *S. lipmanii.* Although the isopenicillin N synthetase-encoding DNA of the present invention was isolated from *S. lipmanii,* the present DNA compounds can be used to construct vectors that drive expression of isopenicillin N synthetase activity in a wide variety of host cells, as the *E. coli* vectors of the present invention illustrate. All organisms that produce penicillins and cephalosporins are believed to utilize the common precursors δ-(L-α-aminoadipyl)-L-cysteinyl-D-valine and isopenicillin N. Therefore, the isopenicillin N synthetase-encoding DNA compounds of the present invention can be used to produce vectors useful for improving efficiency and yield of fermentations involving penicillin and cephalosporin antibiotic-producing organisms of all genera.

The isopenicillin N synthetase-encoding DNA compounds of the present invention were derived from *Streptomyces lipmanii* genomic DNA and were isolated in conjunction with the transcription and translation activating sequence that controls the expression of the isopenicillin N synthetase-encoding genomic DNA. The present invention comprises this novel transcription and translation activating sequence, which can be used to drive expression of genes in Streptomyces, especially *S. lipmanii,* and related organisms.

The present invention also comprises the regulatory signals of the isopenicillin N synthetase gene that are located at the 3' end of the coding strand of the coding region of the gene. These 3' regulatory sequences encode the transcription termination and mRNA polyadenylation and processing signals of the *Streptomyces lipmanii* isopenicillin N synthetase gene. The presence of these signals in the proper position (at the 3' end of the coding strand of the coding region of the gene to be expressed) in an expression vector enhances expression of the product encoded by the vector.

The following section provides a more detailed description of the present invention. For purposes of clarity and as an aid in understanding the detailed description of the invention, as disclosed and claimed herein, the following items are defined below.

2cis—two cistron translational activation sequence

Antibiotic—a substance produced by a microorganism that, either naturally or with limited chemical modification, will inhibit the growth of or kill another microorganism or eukaryotic cell.

Antibiotic Biosynthetic Gene—a DNA segment that encodes an activity that is necessary for a reaction in the process of converting primary metabolites into antibiotics.

Antibiotic-Producing Organism—any organism, including, but not limited to, Aspergillus, Streptomyces, Bacillus, Monospora, Cephalosporium, Penicillium, and Nocardia, that either produces an antibiotic or contains genes that, if expressed, would produce an antibiotic.

Antibiotic Resistance-Conferring Gene—a DNA segment that encodes an activity that confers resistance to an antibiotic.

ApR—the ampicillin resistance-conferring gene.

cI857—a temperature sensitive mutant allele of the cI repressor gene of bacteriophage lambda.

Cloning—the process of incorporating a segment of DNA into a recombinant DNA vector.

Genomic Library—a set of recombinant DNA cloning vectors into which segments of DNA, which substantially represent the entire genome of a particular organism, have been cloned.

HmR—the hygromycin B resistance-conferring gene.

Hybridization—the process of annealing two homologous single-stranded DNA molecules to form a double-stranded DNA molecule, which may or may not be completely base-paired.

IPS or IPNS—Isopenicillin N synthetase; depending on context, may refer to the protein or DNA encoding the protein.

Isopenicillin N Synthetase—an enzyme, also known as cyclase, which catalyzes the formation of isopenicillin N from δ-(L-α-aminoadipyl)-L-cysteinyl-D-valine.

MCS—multiple-cloning site.

mRNA—messenger ribonucleic acid.

pL or λpL—leftward promoter of bacteriophage lambda.

Recombinant DNA Cloning Vector—any autonomously replicating or integrating agent, including, but not limited to, plasmids, comprising a DNA molecule to which one or more additional DNA molecules can be or have been added.

Recombinant DNA Expression Vector—any autonomously replicating or integrating agent, including, but not limited to, plasmids, comprising a transcription and translation activating sequence positioned to drive expression of a DNA segment that encodes a polypeptide or RNA of research or commercial interest.

Recombinant DNA vector—any recombinant DNA cloning or expression vector.

Restriction Fragment—any linear DNA molecule generated by the action of one or more enzymes.

Sensitive Host Cell—a host cell that cannot grow in the presence of a given antibiotic without a DNA segment that confers resistance thereto.

sIPNS—Isopenicillin N synthetase-encoding DNA of *Streptomyces lipmanii*.

S. lip DNA—DNA from *Streptomyces lipmanii*.

TcR—the tetracycline resistance-conferring gene.

Transcription Activating Sequence—a DNA sequence, such as a promoter, that promotes transcription of DNA.

Transformant—a recipient host cell that has undergone transformation.

Transformation—the introduction of DNA into a recipient host cell that changes the genotype and results in a change in the recipient cell.

Translation Activating Sequence—a DNA sequence, such as a ribosome-binding site-encoding sequence, that, when translated into mRNA, promotes translation of mRNA into protein.

BRIEF DESCRIPTION OF THE FIGURES

The restriction site and function maps presented in FIGS. 1-4 of the accompanying drawings are approximate representations of the recombinant DNA vectors discussed herein. The spacing of restriction sites on the map is proportional to the actual spacing of the restriction sites on the vector, but observed restriction site distances may vary somewhat from calculated map distances. The restriction site information is not exhaustive; therefore, there may be more restriction sites of a given type on the vector than actually shown on the map.

DETAILED DESCRIPTION OF THE INVENTION

Figure 1:
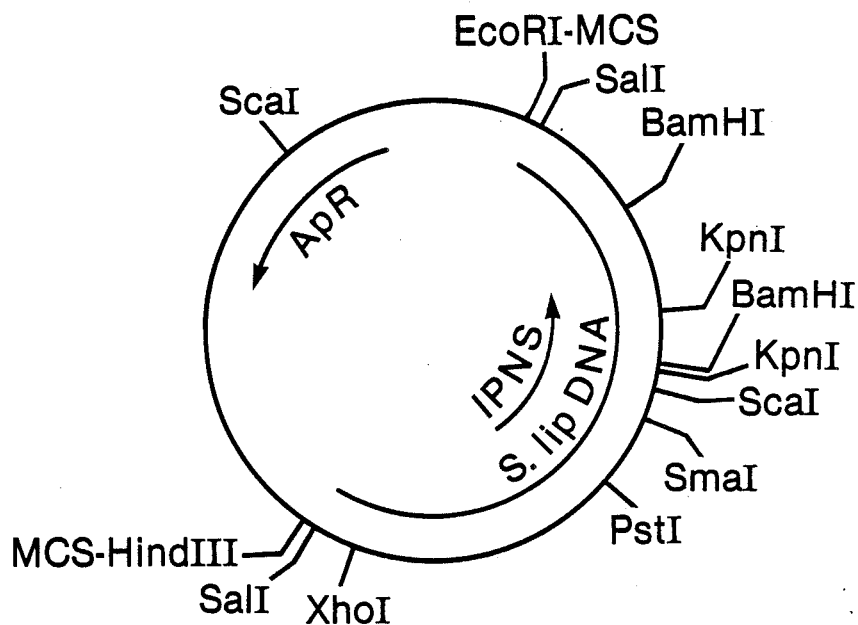
FIG. 1. A restriction site and function map of plasmid pOGO239.

The present invention comprises DNA compounds and recombinant DNA cloning and expression vectors that encode the isopenicillin N synthetase activity of *Streptomyces lipmanii*. The sequence of the *S. lipmanii* isopenicillin N synthetase-encoding DNA is depicted below, together with a portion of the DNA that flanks the 3' and 5' ends of the coding region in the *S. lipmanii* genome. In the depiction, only the "sense" or coding strand of the double-stranded DNA molecule is shown, and the DNA is depicted from left to right in the 5'→3' orientation. The nucleotide sequence is numbered; the numbers appear above the DNA sequence. Immediately below each line of DNA sequence, the amino acid residue sequence of the isopenicillin N synthetase encoded by the DNA is listed from left to right in the amino-terminus→carboxyterminus direction. Each amino acid residue appears below the DNA that encodes it. The amino acid residue sequence is numbered; the numbers appear below the amino acid residue sequence. The first DNA residue of the translation initiation codon is numbered 1; negative numbers refer to the distance in bp (base pairs) upstream from the translation initiation site (zero is not used).

DNA Sequence Encoding The *Streptomyces lipmanii* Isopenicillin N Synthetase
and Corresponding Amino Acid Sequence

```
                                    -40                        -20
       5'-GCAAGACACCGCACGCCATGTCCAGCGCCCACGCCTGGCGCACA 1                              20
       CTCCACGGAGGATGCCATGCCTGTCCTGATGCCGTCGGCCGACGTG
                          Met Pro Val Leu Met Pro Ser Ala Asp Val
                          1                                   10

40                           60
       CCGACGATCGACATCTCCCCCCTGTTCGGGACCGACCCGGACGCC
       Pro Thr Ile Asp Ile Ser Pro Leu Phe Gly Thr Asp Pro Asp Ala
                                                       20

80                    100                         120
       AAGGCGCACGTCGCGCGGCAGATCAACGAGGCCTGCCGCGGTTCG
       Lys Ala His Val Ala Arg Gln Ile Asn Glu Ala Cys Arg Gly Ser
                         30                                  40

140                      160
       GGCTTCTTCTACGCCTCCCACCACGGCATCGACGTGCGGCGGCTG
       Gly Phe Phe Tyr Ala Ser His His Gly Ile Asp Val Arg Arg Leu
                                               50

180                        200
       CAGGACGTGGTCAACGAGTTCCACCGGACCATGACCGACCAGGAG
       Gln Asp Val Val Asn Glu Phe His Arg Thr Met Thr Asp Gln Glu
                               60                              70

220                      240
       AAGCACGACCTGGCGATCCACGCGTACAACGAGAACAACTCGCAT
       Lys His Asp Leu Ala Ile His Ala Tyr Asn Glu Asn Asn Ser His
                                                         80
```

-continued

```
       260                    280                    300
GTGCGCAACGGTTATTACATGGCCCGCCCGGGCCGGAAGACCGTC
Val Arg Asn Gly Tyr Tyr Met Ala Arg Pro Gly Arg Lys Thr Val
             90                                    100

320                    340
GAGTCCTGGTGCTACCTGAACCCGTCGTTCGGCGAGGACCACCCG
Glu Ser Trp Cys Tyr Leu Asn Pro Ser Phe Gly Glu Asp His Pro
                              110

360                    380
ATGATCAAGGCCGGGACGCCGATGCACGAGGTGAACGTCTGGCCG
Met Ile Lys Ala Gly Thr Pro Met His Glu Val Asn Val Trp Pro
             120                                    130

400                    420
GACGAGGAACGCCATCCGGACTTCCGGTCCTTCGGCGAGCAGTAC
Asp Glu Glu Arg His Pro Asp Phe Arg Ser Phe Gly Glu Gln Tyr
                              140

440                    460                    480
TACCGCGAGGTGTTCCGGCTCTCGAAGGTGCTGCTGCTGCGGGGC
Tyr Arg Glu Val Phe Arg Leu Ser Lys Val Leu Leu Leu Arg Gly
             150                                    160

500                    520
TTCGCGCTGGCGCTCGGCAAGCCGGAGGAGTTCTTCGAGAACGAG
Phe Ala Leu Ala Leu Gly Lys Pro Glu Glu Phe Phe Glu Asn Glu
                              170

540                    560
GTCACCGAGGAGGACACCCTCTCCTGCCGATCTCTGATGATCCGG
Val Thr Glu Glu Asp Thr Leu Ser Cys Arg Ser Leu Met Ile Arg
             180                                    190

580                    600
TACCCGTACCTGGATCCGTACCCGGAAGCGGCGATCAAGACGGGC
Tyr Pro Tyr Leu Asp Pro Tyr Pro Glu Ala Ala Ile Lys Thr Gly
                              200

620                    640                    660
CCGGACGGCACCAGGCTCAGCTTCGAGGACCACCTCGACGTGTCG
Pro Asp Gly Thr Arg Leu Ser Phe Glu Asp His Leu Asp Val Ser
             210                                    220

680                    700
ATGATCACCGTCCTGTTCCAGACCGAGGTGCAGAACCTCCAGGTC
Met Ile Thr Val Leu Phe Gln Thr Glu Val Gln Asn Leu Gln Val
                              230

720                    740
GAGACGGTGGACGGGTGGCAGAGCCTGCCGACGTCCGGGGAGAAC
Glu Thr Val Asp Gly Trp Gln Ser Leu Pro Thr Ser Gly Glu Asn
             240                                    250

760                    780
TTCCTGATCAACTGCGGCACCTACCTCGGGTACCTCACGAACGAC
Phe Leu Ile Asn Cys Gly Thr Tyr Leu Gly Tyr Leu Thr Asn Asp
                              260

800                    820                    840
TACTTCCCGGCCCCCAACCACCGGGTCAAGTACGTCAACGCGGAA
Tyr Phe Pro Ala Pro Asn His Arg Val Lys Tyr Val Asn Ala Glu
             270                                    280

860                    880
CGCCTGTCCCTGCCGTTCTTCCTCCACGCCGGGCAGAACAGCGTG
Arg Leu Ser Leu Pro Phe Phe Leu His Ala Gly Gln Asn Ser Val
                              290

900                    920
ATGAAGCCGTTCCACCCGGAGGACACCGGCGACCGGAAGCTCAAC
Met Lys Pro Phe His Pro Glu Asp Thr Gly Asp Arg Arg Leu Asn
             300                                    310

940                    960
CCGGCCGTCACGTACGGGGAGTACCTGCAAGAGGGCTTCCACGCG
Pro Ala Val Thr Tyr Gly Glu Tyr Leu Gln Glu Gly Phe His Ala
                              320
```

```
                980                    1000                      1020
CTGATCGCGAAGAACGTCCAGACCTGAGCAATCGTCAAACTGTGA
Leu Ile Ala Lys Asn Val Gln Thr
                330

1040                     1060
GCTGGTGAAGGAGCTTGCCGGGCACAGCGTGGTGCCCGGCGG-3'.
``` wherein A is deoxyadenyl, G is deoxyguanyl, C is deoxycytidyl, T is thymidyl, ALA is an Alanine residue, ARG is an Arginine residue, ASN is an Asparagine residue, ASP is an Aspartic Acid residue, CYS is a Cysteine residue, GLN is a Glutamine residue, GLU is a Glutamic Acid residue, GLY is a Glycine residue, HIS is a Histidine residue, ILE is an Isoleucine residue, LEU is a Leucine residue, ILE is an Isoleucine residue, LEU is a Leucine residue, LYS is a Lysine residue, MET is a Methionine residue, PHE is a Phenylalanine residue, Pro is a Proline residue, SER is a Serine residue, THR is a Threonine residue, TRP is a Tryptophan residue, TYR is a Tyrosine residue, and VAL is a Valine residue.

Those skilled in the art will recognize that the DNA sequence depicted above is an important part of the present invention. Due to the degenerate nature of the genetic code, which results from there being more than one codon for most of the amino acid residues and stop signal, the amino acid residue sequence of isopenicillin N synthetase depicted above can be encoded by a multitude of different DNA sequences. Because these alternate DNA sequences would encode the same amino acid residue sequence of the present invention, the present invention further comprises these alternate sequences.

These IPNS-encoding sequences can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. An especially preferred method of synthesizing DNA is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the Systec 1450A or ABS 380A DNA Synthesizers.

In addition to the IPNS-encoding DNA sequences discussed above, there could be genetic variants of the isopenicillin N synthetase-encoding DNA of the present invention. These genetic variants would share substantial DNA and amino acid residue sequence homology with the compounds of the present invention and would have similar, if not identical, activity, but would differ somewhat in nucleotide sequence from the specific, illustrative compounds of the invention. These genetic variants are equivalent to the compounds of the present invention and can be obtained by virtue of homology with the IPNS-encoding DNA sequences of the present invention.

The isopenicillin N synthetase activity-encoding DNA compounds of the present invention were isolated from a strain of *Streptomyces lipmanii*. A genomic library of the total genomic DNA of the *S. lipmanii* strain was constructed and examined for the presence of sequences homologous to a deoxyribooligonucleotide probe. This probe was constructed in accordance with information obtained about the aminoterminal amino acid sequence of the *S. lipmanii* isopenicillin N synthetase, with knowledge of the genetic code, and with knowledge of codon usage preferences of Streptomyces. Several of the vectors of the genomic library were identified that were nearly homologous to the deoxyribooligonucleotide. DNA sequencing revealed which vectors encoded the *S. lipmanii* isopenicillin N synthetase.

The *Streptomyces lipmanii* isopenicillin N synthetase gene was then cloned into another vector to yield plasmid pOGO239, which was transformed into *E. coli* K12 JM109 host cells. The *E. coli* K12 JM109/pOGO239 transformants were deposited and made part of the stock culture collection of the Northern Regional Research Laboratories (NRRL), Agricultural Research Service, U.S. Department of Agriculture, Peoria, Illinois 61604, under the accession number NRRL B-18250. A restriction site and function map of plasmid pOGO239 is presented in FIG. 1 of the accompanying drawings.

Plasmid pOGO239 can be isolated from *E. coli* K12 JM109/pOGO239 by the procedure described in Example 1. Plasmid pOGO239 serves as useful starting material for vectors of the invention. Plasmid pOGO239 contains the intact *Streptomyces lipmanii* IPNS gene, which can be isolated from the plasmid on an ~2.8 kb SalI restriction fragment. Plasmid pOGO239 was used as starting material in the construction of a plasmid, designated pOGO249, that drives high-level expression of isopenicillin N synthetase in *E. coli*. To facilitate manipulation of the *S. lipmanii* IPNS coding sequence as well as any manipulations of the native Streptomyces promoter sequence, a restriction enzyme NdeI recognition sequence was created at position −3 to +3 of the *S. lipmanii* IPNS DNA coding sequence.

Figure 2:
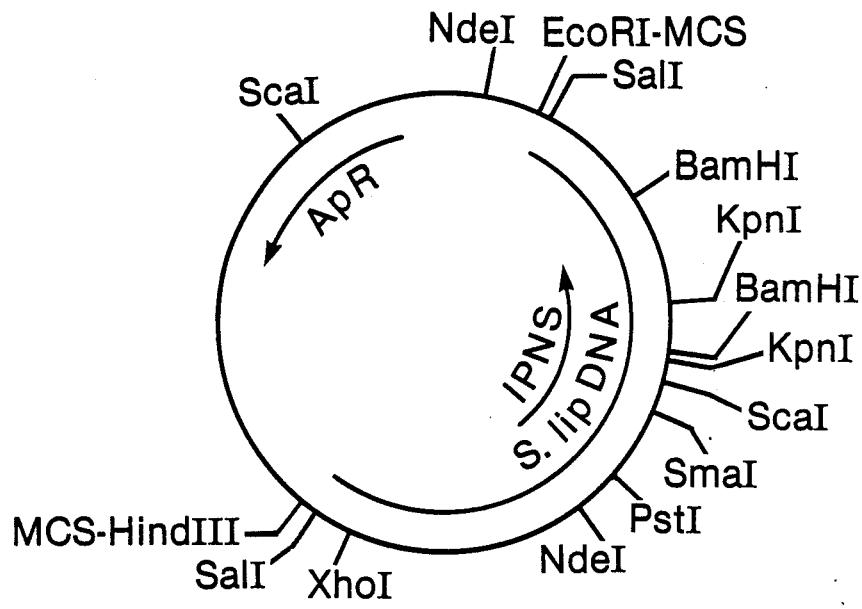
FIG. 2. A restriction site and function map of plasmid pOGO246.
Figure 4:
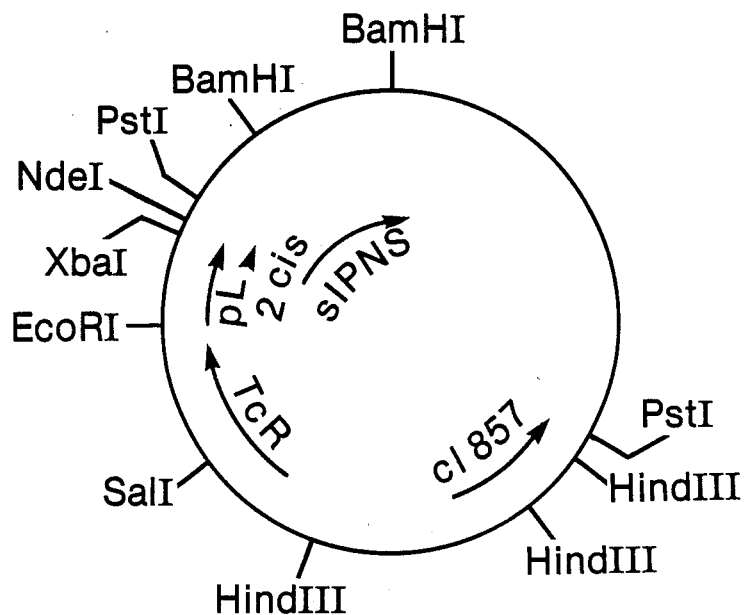
FIG. 4. A restriction site and function map of plasmid pOGO249.

The creation of the NdeI site was done by M13 site-directed mutagenesis techniques and involved changing DNA bases −1 to −3 from GCC to CAT. One skilled in the art will recognize that DNA mutagenesis techniques are commonly used to introduce restriction enzyme recognition sites into DNA sequences and that in this case the encoded amino acid sequence was not changed. The mutagenesis and intermediate constructs are described in greater detail in Examples 2 through 4. The resulting plasmid, designated pOGO246 and described more fully in Example 4, differs from plasmid pOGO239 only in the presence of a restriction enzyme NdeI site. A restriction site and function map of plasmid pOGO246 is presented in FIG. 2 of the accompanying drawings. Intermediate plasmid pOGO246 was then used to construct the expression vector pOGO249. Plasmid pOGO249 is described below and in more detail in Example 5. A restriction site and function map of plasmid pOGO249 is presented in FIG. 4 of the accompanying drawings.

Figure 3:
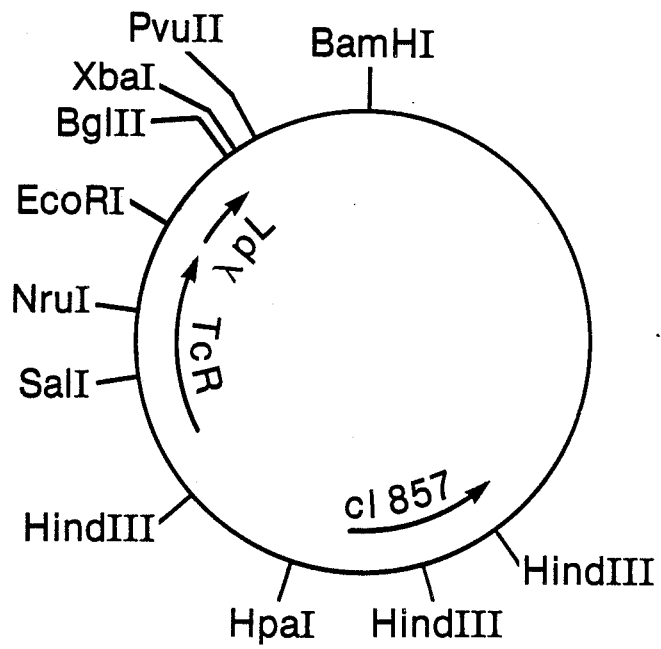
FIG. 3. A restriction site and function map of plasmid pCZR111.

Plasmid pOGO249 was constructed by inserting the *Streptomyces lipmanii* IPNS coding sequence into plasmid pCZR111, an expression vector that comprises the lambda pL transcription and translation activating sequence, the cI857 temperature sensitive repressor gene, a tetracycline resistance-conferring gene, and DNA sequences encoding vector replication functions. The use of the type of temperature-inducible expression system present on plasmid pCZR111 is described and disclosed in U.S. patent application Ser. No. 769,221, filed Aug. 26, 1985, attorney docket number X-6638. Essentially, at low temperature of about 30° C. the cI857 gene product represses transcription driven by the pL promoter, but when the temperature is raised to ~42° C., the cI857 gene product is inactivated and the pL promoter becomes active. Plasmid pCZR111 is available from the NRRL under the accession number NRRL B-18249. A restriction site and function map of plasmid pCZR111 is presented in FIG. 3 of the accompanying drawings.

Plasmid pOGO249 comprises the lambda pL promoter and a 2-cistron translation activating sequence positioned to drive expression of the protein-coding sequence of the *Streptomyces lipmanii* isopenicillin N synthetase gene. Two-cistron constructions are generally described in Schoner et al., 1984, Proc. Natl. Acad. Sci. 81:5403–5407 and Schoner et al., 1986, Proc. Natl. Acad. Sci. 83:8506–8510. The IPNS coding sequences contained in plasmid pOGO249 originated from the ~1.2 kb NdeI-BamHI restriction fragment of plasmid pOGO246.

At temperatures of about 42° C., *E. coli* K12 JM109/pOGO249 cells express isopenicillin N synthetase at high levels, approaching 25% of the total cell protein. Crude cell extracts from these *E. coli* K12 JM109/pOGO249 transformants are able to catalyze the conversion of δ-(L-α-aminoadipyl)-L-cysteinyl-D-valine into isopenicillin N, whereas cell extracts from nontransformed *E. coli* K12 JM109 cells cannot catalyze this conversion. The method of assay for the conversion reaction is described in Example 6.

Plasmid pOGO249 provides an efficient means of producing large amounts of isopenicillin N synthetase in *E. coli*. Because *E. coli* transformants containing plasmid pOGO249 express isopenicillin N synthetase at levels approaching 25% of total cell protein, and because culturing *E. coli* is less complex than culturing organisms that naturally produce isopenicillin N synthetase, *E. coli*/pOGO249 transformants can be used to produce recombinant isopenicillin N synthetase more efficiently and economically than non-recombinant or "natural" isopenicillin N synthetase producers. The *E. coli* K12/pOGO249 transformants of the present invention, by producing such high levels of isopenicillin N synthetase, allow for the isolation of the isopenicillin N synthetase encoded on the *Streptomyces lipmanii* genome in substantially pure form.

Isopenicillin N synthetase can be used to produce isopenicillin N from δ-(L-α-aminoadipyl)-L-cysteinyl-D-valine in a cell-free system, as described in Example 6. Isopenicillin N is not only a useful antibiotic but also the starting material for the production of such important antibiotics as penicillin N, cephalexin, and other cephalosporins as described in U.S. Pat. No. 4,307,192. Another important use of isopenicillin N synthetase is for condensing tripeptides other than δ-(L-α-aminoadipyl)-L-cysteinyl-D-valine into novel β-lactam derivatives.

Cell-free extracts of penicillin-producing organisms can be used to synthesize unnatural (not produced in nature) β-lactams. The *E. coli* expression vectors of the present invention provide an inexpensive and efficient method of obtaining isopenicillin N synthetase, both in crude cell extracts and in substantially purified form, which can be used in vitro to condense tripeptides that do not naturally occur in nature to form novel antibiotics or antibiotic core structures.

Plasmid pOGO249 is especially preferred for driving expression of IPNS in *E. coli* not only because of the high expression levels achieved when using the plasmid but also because of the selectable marker present on the plasmid. Many recombinant DNA vectors encode a β-lactamase, so that cells transformed with such vectors can grow in the presence of certain β-lactam antibiotics, such as ampicillin. However, if one desires to use a cell-free extract containing IPNS for purposes of constructing β-lactams, one would not want the extract to contain β-lactamase activity. Thus, plasmid pOGO249 does not encode a β-lactamase for a selectable marker but rather encodes the tetracycline resistance-conferring gene, the gene product of which is non-reactive with β-lactams.

The IPNS expression vectors of the present invention are not limited to a particular selectable marker. Those skilled in the art recognize that many selectable markers are suitable for use on IPNS expression vectors. Such selectable markers include genes that confer kanamycin resistance, i.e., a selectable marker on Tn903, and genes that confer chloramphenicol resistance, i.e., a selectable marker on plasmids pACYC184 and pBR325.

The vectors of the present invention include vectors that drive expression of IPNS in β-lactam producing organisms. For obvious reasons, the β-lactamase gene is not preferred for use as a selectable marker in a β-lactam-producing microorganism. Nevertheless, the β-lactamase gene might be present on vectors of the present invention designed for use in β-lactam-producing organisms, such as Penicillium or Cephalosporium, simply because of its utility as a selectable marker in *E. coli*. Many vectors designed for β-lactam-producing organisms also are constructed so as to replicate in *E. coli* for ease of plasmid preparation. Certain β-lactam-producing organisms, such as *C. acremonium*, are eukaryotic cells, but the prokaryotic β-lactamase gene derived from plasmid pBR322 seems to function in some eukaryotic host cells. See Marczynski and Jaehning, 1985, Nuc. Acids Res. 13(23):8487–8506 and Breunig et al., 1982, Gene 20:1–10. To avoid the possibility of introducing a β-lactamase gene that could possibly express in an organism transformed to obtain greater β-lactam-producing ability, the present invention also comprises vectors that utilize a selectable marker other than the β-lactamase gene, such as a chloramphenicol acetyltransferase-encoding gene.

As stated above, a β-lactamase gene is generally not suitable for use as a selectable marker in penicillin or cephalosporin antibiotic-producing organisms, such as *Cephalosporium acremonium, Penicillium chrysogenum, Streptomyces clavuligerus,* or *Aspergillus nidulans,* nor do these organisms encode an endogenous β-lactamase. However, many *E. coli* strains, even those sensitive to β-lactams, do encode and express, at low levels, an endogenous β-lactamase, i.e., the *E. coli* ampC gene product. See Juarin et al., 1981, Proq. Natl. Acad. Sci. 78(8):4897–4901 and Grundström et al., 1982, Proc. Natl. Acad. Sci. 79:1111–1115. The presence of the ampC gene product in crude cell extracts of recombinant *E. coli* cells containing an IPNS expression vector could lead to degradation of β-lactams prepared using that extract. To avoid such degradation, E. coli K12 RV308 was subjected to mutagenesis to obtain a strain, designated E. coli K12 A85892, that does not express a β-lactamase activity (unless the activity is encoded on a recombinant vector present in the cell). E. coli K12 A85892 can be obtained from the Northern Regional Research Center under the accession number NRRL B-18096.

The search for unnatural tripeptides that will serve as substrates for isopenicillin N synthetase can be complemented by a search for mutant isopenicillin N synthetases that will accept unnatural tripeptides as substrate. The present invention provides the starting material for such a search for a mutant isopenicillin N synthetase. E. coli is the best host for mutational cloning experiments, and the E. coli expression vectors of the present invention can be readily mutated by procedures well known in the art, such as, for example, treatment with radiation (X-ray or UV) or chemical mutagens (such as ethylmethanesulfonate, nitrosoguanidine, or methyl methanesulfonate) or site-specific mutagenesis, to obtain mutant enzymes that recognize unnatural tripeptides as substrate and catalyze the condensation of those unnatural tripeptides to unnatural β-lactams.

The present invention is not limited to the particular vectors exemplified herein. The DNA compounds of the present invention encode the isopenicillin N synthetase activity of *Streptomyces lipmanii* and can be used to isolate homologous DNA compounds from other Streptomyces strains that encode genetic variants of the isopenicillin N synthetase of the present invention. Consequently, the present invention comprises DNA compounds homologous to the isopenicillin N synthetase-encoding DNA on plasmids pOGO239, pOGO246, and pOGO249 that encode isopenicillin N synthetase activity.

Furthermore, the DNA compounds of the present invention can be used to construct expression vectors that drive expression of isopenicillin N synthetase in any host cell. These vectors can be constructed for any host cell by choosing elements that function in the host cell of choice. Such elements might encode vector replication or integration functions and a transcription and translation activating sequence to drive expression of the isopenicillin N synthetase activity.

The E. coli expression vectors of the invention are not limited to the specific vectors exemplified herein. The present invention comprises any E. coli expression plasmid or vector that drives expression of isopenicillin N synthetase in E. coli. Thus, the present invention comprises expression vectors that drive expression of isopenicillin N synthetase and utilize a replicon functional in E. coli, such as, for example, a runaway replicon or a replicon from such plasmids as pBR322, pACYC184, F, ColV-K94, R1, R6-5, or R100. Nor is the present invention solely limited to plasmid vectors, for the present invention also comprises expression vectors that express isopenicillin N synthetase activity and utilize integration or viral replication to provide for replication and maintenance in the host cell.

The present invention is not limited to a particular transcription and translation activating sequence to drive expression of the isopenicillin N synthetase activity-encoding DNA. The present invention comprises the use of any transcription and translation activating sequence to express isopenicillin N synthetase in E. coli. Many transcription and translation activating sequences that function in E. coli are known and are suitable for driving expression of isopenicillin N synthetase activity in E. coli. Such transcription and translation activating sequences include, but are not limited to, the lpp, lac, trp, tac, λp$_L$, and λp$_R$ transcription and translation activating sequences.

In addition to the various E. coli replicons and transcription and translation activating sequences exemplified above, replicons and transcription and translation activating sequences from other organisms can be ligated to the present isopenicillin N synthetase-encoding DNA compounds to form expression vectors that drive expression of isopenicillin N synthetase activity in host cells in which the replicon and activating sequence function. Although E. coli is the host best suited for isopenicillin N synthetase production and subsequent purification for in vitro use, vectors that drive expression of isopenicillin N synthetase activity in host cells other than E. coli are also useful, especially for purposes of increasing the β-lactam antibiotic-producing ability and efficiency of a given organism.

A variety of organisms produce β-lactam antibiotics. The following Table presents a non-comprehensive list of β-lactam antibiotic-producing organisms.

TABLE I

| β-Lactam Antibiotic-Producing Organisms | |
|---|---|
| Organism | Antibiotic |
| Agrobacterium | various β-lactams |
| Aspergillus nidulans | various β-lactams |
| Cephalosporium acremonium | penicillins and cephalosporins |
| Chromobacterium | various β-lactams |
| Gluconobacter | various β-lactams |
| Nocardia lactamdurans | cephamycin C |
| uniformis | nocardicin |
| Penicillium chrysogenum | various penicillins and other β-lactams |
| Serratia | various β-lactams |
| Streptomyces antibioticus | clavulanic acid |
| argenteolus | asparenomycin A, MM 4550, and MM 13902 |
| cattleya | thienamycin |
| chartreusis | SF 1623 and cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxycephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |

TABLE I-continued

| β-Lactam Antibiotic-Producing Organisms | |
|---|---|
| Organism | Antibiotic |
| viridochromogenes | cephamycin A and B |
| wadayamensis | WS-3442-D |

Many of the foregoing β-lactam antibiotic-producing organisms are used in the pharmaceutical industry for purposes of antibiotic production. The antibiotic-producing ability of these organisms can be increased and made more efficient by increasing the intracellular concentration of rate-limiting antibiotic biosynthetic enzymes during the fermentation. The isopenicillin N synthetase activity-encoding DNA compounds of the present invention can be used to construct expression vectors. When these IPNS expression vectors are transformed into a host cell that produces a β-lactam antibiotic via an intermediate reaction involving isopenicillin N synthetase activity, the intracellular concentration of isopenicillin N synthetase activity is increased. Provided that IPNS activity is the ratelimiting factor of the β-lactam biosynthesis in the untransformed host cell, host cells containing these IPNS expression vectors produce more β-lactam antibiotic than their untransformed counterparts.

A vector that will increase the intracellular concentration of isopenicillin N synthetase activity of a given host cell into which the vector is transformed requires the following elements: (1) an isopenicillin N synthetase activity-encoding DNA compound; (2) a transcription and translation activating sequence that not only functions in the host cell to be transformed, but also is positioned in the correct orientation and position to drive expression of the isopenicillin N synthetase activity-encoding DNA; and (3) replication or integration functions that provide for maintenance of the vector in the host cell. The frequency of integration of a DNA vector often is quite dependent on activities encoded by the host cell; however, it is often observed that certain DNA sequences (i.e., sequences from viruses and phages that facilitate integration and sequences homologous to the host's genomic DNA), when present on a recombinant DNA vector facilitate integration. Of course, an IPNS expression vector could also comprise an antibiotic resistance-conferring gene or some other element that provides a means of selecting for host cells which contain the vector, but such selectable elements may be neither necessary nor desired when the vector integrates into the chromosomal DNA of the host cell.

A variety of the plasmids of the present invention are useful for increasing the intracellular concentration of isopenicillin N synthetase activity in a β-lactam antibiotic-producing cell. Plasmid pOGO239 comprises the intact isopenicillin N synthetase gene of *Streptomyces lipmanii*, so transformation of *S. lipmanii* with plasmid pOGO239 leads to increased copy number of the isopenicillin N synthetase gene and thus to increased intracellular concentration of the enzyme. The intact *S. lipmanii* isopenicillin N synthetase gene of the invention is also useful in such host cells as Aspergillus, Cephalosporium, and Penicillium. Consequently, transformation of these host cells with a plasmid of the invention such as plasmid pOGO239 would lead to increased copy number of the isopenicillin N synthetase gene and to increased intracellular concentration of the enzyme.

Because the IPNS gene of the invention was isolated from a Streptomyces host cell, the IPNS gene is particularly well-suited for use in expression vectors designed to drive high-level expression of IPNS in Streptomyces. The literature is replete with techniques for constructing Streptomyces expression vectors and for transforming Streptomyces host cells. See, for instance, Garcia-Dominguez et al., 1987, Applied and Environmental Microbiology 53(6):1376–1381. The IPNS gene of the invention can be readily incorporated into an expression vector that comprises a Streptomyces replicon, and a variety of known Streptomyces replicons are available for such use. Table II is an illustrative, but not comprehensive, listing of Streptomyces plasmids from which Streptomyces replicons can be obtained. Those skilled in the art recognize that, so long as the replicon function is not disrupted, all or part of the plasmids listed in the Table may be used to construct vectors that contain the IPNS gene of the present invention. The plasmid-containing host and depository accession number are also listed in Table II.

TABLE II

| Streptomyces Plasmids | | |
|---|---|---|
| Plasmid | Host | Accession Number |
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | *Streptomyces* 3022A | NRRL 11441 |
| SLP1 | *Streptomyces lividans* | NCIB* 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC** 39155 |

*National Collection of Industrial Bacteria (NCIB), Torry Research Station, Post Office Box 31, 135 Abbey Road, Aberdeen AB98DG, Scotland, United Kingdom.
**American Type Culture Collection, Rockville, MD 20852.

The *Streptomyces lipmanii* IPNS coding sequence of the invention can also be put under the control of transcription and translation activating sequences derived from Penicillium, Cephalosporium, or any other host cell to construct a recombinant gene especially for use in the given organism. U.S. patent application Ser. No. 06/895,008, filed Aug. 8, 1986, attorney docket No. X-6722B, incorporated herein by reference, discloses the transcription and translation activating sequences of the *C. acremonium* IPNS gene, which can be fused to the *S. lipmanii* IPNS coding sequence of the present invention to create a recombinant IPNS gene that drives expression (when incorporated into an expression vector and the vector introduced into Cephalosporium) of the *S. lipmanii* IPNS coding sequence in Cephalosporium. Likewise, U.S. patent application Ser. No. 06/801,523, filed Nov. 25, 1985, attorney docket No. X-6932, incorporated herein by reference, discloses the transcription and translation activating sequences of the *P. chrysogenum* IPNS gene, which can be used as described above to construct Penicillium vectors that drive expression of the *S. lipmanii* IPNS coding sequence.

The present invention results from the cloning of an intact, functional, *Streptomyces lipmanii* DNA sequence that encodes not only the amino acid residue sequence of isopenicillin N synthetase but also the transcription and translation activating sequence necessary to drive expression of isopenicillin N synthetase in *S. lipmanii*. Likewise, the isopenicillin N synthetase gene of the present invention comprises the sequences located downstream of the coding region that are responsible for terminating transcription and for providing the mRNA polyadenylation and processing signals. These 5' and 3' regulatory elements comprise an important aspect of the present invention.

Because plasmids pOGO239 and pOGO246 comprise ~1.0 kb of the genomic DNA that was located upstream of the isopenicillin N synthetase-encoding DNA in the *S. lipmanii* genome, plasmids pOGO239 and pOGO246 necessarily comprise the transcription and translation activating sequence of the *S. lipmanii* isopenicillin N synthetase gene. Most transcription and translation activating sequences are encoded upstream of the DNA to be activated, although some ribosomal RNA-encoding DNA sequences are activated by transcription activating sequences that are not located upstream of the coding region. "Upstream," in the present context, refers to DNA in the 5' direction from the 5' end of the coding strand of the isopenicillin N synthetase-encoding DNA.

The *Streptomyces lipmanii* transcription and translation activating sequence encoded on plasmid pOGO239 is correctly positioned to drive expression of the isopenicillin N synthetase activity-encoding DNA. In the construction of plasmid pOGO239, no deletions or insertions affecting the transcription and translation activating sequence were introduced in the DNA flanking the 5' end of the coding strand of the isopenicillin N synthetase activity-encoding DNA. Because the *S. lipmanii* transcription and translation activating sequence located on plasmid pOGO239 can be used to drive expression of a wide variety of DNA sequences, the activating sequence comprises an important part of the present invention. The activating sequence of the *S. lipmanii* isopenicillin N synthetase gene can be isolated on the ~1.2 kb SalI-PstI restriction fragment located immediately upstream of and adjacent to the isopenicillin N synthetase activity-encoding DNA on plasmid pOGO239. The PstI site encodes amino acid residues 55 and 56 of the isopenicillin N synthetase protein, so the amino terminal coding region of the isopenicillin N synthetase is also contained on this SalI-PstI fragment. Any restriction fragment that comprises the aforementioned ~1.2 kb SalI-PstI restriction fragment necessarily comprises the *S. lipmanii* transcription and translation activating sequence of the present invention.

The *Streptomyces lipmanii* transcription and translation activating sequence can be used to drive expression of any DNA sequence in *S. lipmanii* and other Streptomyces species. The transcription and translation activating sequence from the *S. lipmanii* isopenicillin N synthetase gene can be fused to protein coding regions in several useful ways. For example, the activating sequence can be isolated on an ~1 kb SalI-NdeI restriction fragment from plasmid pOGO246. Just as plasmid pOGO246 is derived from plasmid pOGO239 via site-directed mutagenesis to create an NdeI restriction site at the translation initiation site, so can any protein-coding sequence of interest be adapted to contain compatible ends for convenient ligation to the *S. lipmanii* activating sequence. Such strategies will be readily apparent to those skilled in the art and may be different for different protein-coding sequences. An exemplary strategy is outlined in Example 5, which describes the protocol for fusing the *S. lipmanii* isopenicillin N synthetase protein-coding sequence to the *E. coli* transcription and translation activating sequence on plasmid pCZR111.

Similar strategies allow the *Streptomyces lipmanii* isopenicillin N synthetase protein-coding sequence to be joined to transcription and translation activating sequences from any organism of interest. For example, an activating sequence from the organism of interest can be reconstructed so that the 5'-ATG transcription initiation site is nested within an NdeI restriction site, 5'-CATATG-3'. The *S. lipmanii* isopenicillin N synthetase protein-coding sequence of plasmid pOGO246 can then be simply joined to the promoter to produce a hybrid gene that will drive expression of the *S. lipmanii* isopenicillin N synthetase in any organism in which the activating sequence functions. The flanking ends of the hybrid gene can be similarly adapted, if necessary, to allow insertion of the hybrid gene into a vector suitable for the organism of interest.

Plasmid pOGO239 also comprises the 3' regulatory sequences of the *Streptomyces lipmanii* isopenicillin N synthetase gene. Usually, the sequences responsible for transcription termination, mRNA polyadenylation, and mRNA processing are encoded within the region ~500 bp downstream of the stop codon of the coding region of a gene. Therefore, the ~0.94 kb KpnI-SalI restriction fragment that comprises the isopenicillin N synthetase carboxy-terminal-encoding DNA and downstream sequences also comprises the transcription termination and mRNA polyadenylation and processing signals of the *S. lipmanii* isopenicillin N synthetase gene.

The transcription termination sequence in plasmid pOGO239 can be appended to other recombinant gene constructions to facilitate transcription termination in those constructs. For example, a KpnI restriction site (located at about the codons for amino acid residues 260 and 261 of the *S. lipmanii* isopenicillin N synthetase amino acid residue sequence) is convenient for isolating the transcription termination sequences, because the KpnI cleavage site is near the translation termination site (translation terminates after amino acid residue 333). A SalI restriction enzyme recognition site located ~800 bp downstream of the translation termination site provides a convenient distal or downstream end, allowing the transcription terminator to be isolated on an ~940 bp KpnI-SalI restriction fragment from plasmid pOGO239.

Expression of a given DNA sequence on a recombinant DNA expression vector can be enhanced by placing a transcription termination and mRNA polyadenylation and processing signal at the 3' end of the coding strand of the coding region to be expressed. The present invention provides a transcription termination and mRNA polyadenylation and processing signal that can be used for the purposes of increasing expression of any gene product from a recombinant DNA vector in Streptomyces and related host cells.

The following Examples are provided to further illustrate and exemplify, but are in no way intended to limit the scope of, the present invention.

EXAMPLE 1

A. Culture of *E. coli* K12 JM109/pOGO239

A lyophil of *E. coli* K12 JM109/pOGO239 is obtained from the Northern Regional Research Laboratories (NRRL), Peoria, IL 61604, under the accession number NRRL B-18250. The lyophil can be directly used as the "culture" in the process described below.

One liter of L-broth (10 g tryptone, 10 g NaCl, and 5 g yeast extract per liter) containing 100 μg/mL ampicillin was inoculated with a culture of *E. coli* K12

JM109/pOGO239 and incubated with aeration at 37° C. overnight (15–18 hours).

B. Isolation of Plasmid pOGO239

The culture prepared in Example 1A was centrifuged in a Beckman JS-5.2 rotor (Beckman Instruments, Inc., Spinco Division, Palo Alto, CA 94304) at 5200 rpm for 25 minutes at 4° C. The resulting supernatant was discarded. The cell pellet was resuspended in 28 mL of a solution of 25% sucrose and 50 mM EDTA. About 1 mL of a solution of 20 mg/mL lysozyme in 50% glycerol and 0.25 M Tris-HCl, pH=8.0, and about 1.5 mL of 0.5 M EDTA, pH=8.0, were added to and mixed with the cell suspension. The resulting mixture was incubated on ice for 15 minutes. Three mL of lysing solution (prepared by mixing 3 mL of 10% Triton-X100; 75 mL of 0.25 M EDTA; pH=8.0; and 7 mL of water) were added to the lysozyme-treated cells with gentle mixing. The resulting solution was incubated on ice for another 15 minutes.

The cellular debris was removed from the solution by centrifugation at 17,000 rpm in a Beckman JA-17 rotor for about 45 minutes at 4° C. About 28.6 g of CsCl and ~1 mL of a 5 mg/mL ethidium bromide solution were added to the ~30 mL of supernatant. Then, the volume was adjusted to 40 mL with water and the solution decanted into a VTi50 ultracentrifuge tube (Beckman). The tube was sealed, and the solution was centrifuged in a VTi50 rotor at 49,500 rpm for ~18 hours. The resulting plasmid band, visualized with ultraviolet light, was isolated, extracted with salt-saturated isopropanol to remove the ethidium bromide, and dialysed against three changes of ~20 volumes of TE buffer (10 mM Tris-HCl, pH=7.5, and 1 mM EDTA). The dialysate was collected; then, two volumes of ethanol and 0.05 volumes of 3 M sodium acetate solution were added. The ethanol mixture was cooled to −20° C., and the plasmid DNA was pelleted by centrifugation in a JA-17 rotor (Beckman) at 10,000 rpm for 30 minutes at −10° C. The resulting pellet was resuspended in ~1 mL of TE buffer and then extracted with an equal volume of a phenol-chloroform mixture (1:1, v/v). The DNA in the aqueous phase was recovered by the addition of 0.1 volume of 3 M NaOAc and 2 volumes of ethanol, followed by incubation at −20° C. for ~30 minutes and centrifugation at 15,000 rpm for 20 minutes. The resulting DNA pellet was rinsed first with 70% ethanol and then with 100% ethanol and dried.

The ~1.5 mg of plasmid pOGO239 DNA obtained by this procedure was suspended in 1.5 mL of 0.1X TE buffer and stored at −20° C. A restriction site and function map of plasmid pOGO239 is presented in FIG. 1 of the accompanying drawings.

EXAMPLE 2

Construction of Phage mOGO244

One skilled in the art will realize that identical plasmid constructs can be achieved employing different methods and sources of gene sequences. Phage mOGO244 was constructed by "shotgun" cloning of a SalI restriction digest of a lambda EMBL3 clone into a SalI-cut M13 vector. The lambda EMBL3 clone originated from a *Streptomyces lipmanii* genomic EMBL3 library and was identified by plaque hybridization using a "guessmer" DNA probe designed on the basis of the amino-terminal amino acid residue sequence of purified *S. lipmanii* IPNS and species codon-usage bias. The desired phage M13 clone was identified using the "guessmer" probe in a plaque hybridization procedure. Because of the present invention, however, the construction of mOGO244 is greatly simplified, primarily because plasmid pOGO239 can be used as the source of the *S. lipmanii* IPNS gene. The M13-derived phage mOGO244 was a useful intermediate in the site-specific mutagenesis carried out to create an NdeI restriction enzyme recognition site in the *S. lipmanii* IPNS coding sequence.

A. Preparation of SalI-Digested Plasmid pOGO239

Approximately 25 μg of the plasmid pOGO239 DNA in 25 μl 1 0.1X TE buffer, as prepared in Example 1B, are added to and mixed with 40 μl of 10X SalI buffer (1.5 M NaCl; 100 mM Tris-HCl, pH=7.5; and 100 mM $MgCl_2$), 335 μl of glass-distilled water, and 5 μl (~50 units) of restriction enzyme SalI. Unless otherwise noted, restriction enzymes were obtained from New England Biolabs, 32 Tozer Road, Beverly, MA 01915. Unit definitions herein correspond to the particular manufacturer's unit definitions. The resulting reaction is incubated at 37° C. for 90 minutes. The reaction is then extracted with an equal volume of $CHCL_3$. The DNA in the aqueous phase is concentrated by ethanol precipitation as follows. One-tenth volume of 3 M sodium acetate (NaOAc) solution and 2.5 volumes of ethanol are added to the DNA solution, which is then mixed and incubated at −20° C. for ≧1 hour. If desired, tRNA can be added to the ethanol-DNA solution to facilitate precipitation of the DNA. After incubation at −20° C., the solution is centrifuged for 20 minutes at 15,000 rpm. The DNA pellet is rinsed first with 70% ethanol and then with 100% ethanol and dried. The pellet is resuspended in ~20 μl of 0.1X TE buffer and constitutes ~10 μg of SalI-digested plasmid pOGO239 DNA. The SalI-digested DNA is stored at −20° C.

B. Preparation of SalI-digested Vector M13mp19

About 2.5 μg of phage M13mp19 DNA (available from New England Biolabs (NEB)) was digested in 100 μl of SalI buffer with 1 μl (~20 units) of restriction enzyme SalI for 90 minutes at 37° C. The reaction mixture was extracted with phenol:chloroform and the DNA, in the aqueous phase, concentrated by ethanol precipitation. The DNA pellet was resuspended in 20 μl of 0.1X TE buffer and constituted ~2 μg of the desired SalI-digested M13mp19 vector. The vector DNA obtained was stored at −20° C.

C. Construction of Phage mOGO244

One μl of SalI-digested plasmid pOGO239 DNA and 1 μl of SalI-digested vector M13mp19 are ligated in a 20 μl reaction containing the DNA fragments, 2 μl of 10X ligase buffer (0.5 M Tris-HCl, pH 7.5, and 100 mM $MgCl_2$), 2 μl of 5 mM ATP, 1 μl of 6 μg/μl BSA, 12 μl of glass-distilled water, and 1 μl (1 Weiss unit) of T4 DNA ligase (Boehringer-Mannheim Biochemicals (BMB), P.O. Box 50816, Indianapolis, IN 46250). The reaction is incubated ~18 hours at 15° C. The ligated DNA constitutes the desired phage mOGO244 along with other ligation products.

D. Transformation of *E. coli* K12 JM109 With Phage mOGO244

Competent *E. coli* K12 JM109 ("Epicurean Coli ™") were purchased from Stratagene (3770 Tansy Street, San Diego, CA 92121) and transformed with a ligation reaction constituting phage mOGO244 (such as described in Example 2C) in substantial accordance with the manufacturer's directions, except that the DNA was in a volume of 20 µl and no dilution into medium or expression time was necessary. Post-transformation, the cells were distributed in ~1, 10, 20, 40 and 50 µl aliquants to 13×100 mm sterile glass tubes containing 0.25 mL/tube *E. coli* K12 JM109 in logarithmic growth phase. To these tubes were added 3 mL of top agar (L broth with 0.8% agar kept molten at 45° C.). The cell-top agar mixture was then plated on L-agar plates containing 40 µg/mL 5-bromo-4-chloro-3-indolyl-β-D-galactoside (X-gal) and 0.1 M isopropylthio-β-galactoside (IPTG), and the plates were incubated at 37° C. overnight. (For more detailed descriptions and explanations of M13 procedures, see *M13 Cloning/Dideoxy Sequencing Instruction Manual*, Bethesda Research Laboratories (BRL), Life Technologies, Inc., Gaithersburg, MD 20877.) Transformants are identified by insertional inactivation of β-galactosidase activity (colorless plaque phenotype) and restriction enzyme analysis of replicative form (RF) DNA. For screening purposes, clear plaques are plugged from the plate overlay with a Pasteur pipette into 3 mL per plaque of early logarithmic growth phase *E. coli* K12 JM109. Cultures are incubated from 6 to 18 hours at 37° C. with aeration.

Following this incubation, 1.5 mL of each culture are pelleted in separate 1.5 mL Eppendorf tubes. The supernatants are decanted into fresh tubes and stored at 4° C. to serve as a source of phage inoculum. Replicative form DNA is prepared from the cell pellets in substantial accordance with the teaching of the alkaline plasmid preparation procedure of Birnboim and Doly, 1979, *Nuc. Acid Res.* 7(6): 1513–1523, with the following exceptions. The procedure is scaled up such that b 1.5× volumes of Solutions I, II, and III are used, and the cleared lysate is extracted once with an equal volume of CHCl₃. The DNA is then precipitated by the addition of 0.4 volumes of isopropanol and incubation at room temperature for 20 minutes. The DNA is collected by centrifugation and then precipitated with ethanol out of 0.3 M NaOAc. The analysis of the restriction pattern of the RF DNA is facilitated by the existence of an asymetric XhoI restriction enzyme recognition site that is not only diagnostic for the presence of the desired insert but also can be used to orient the insert sequence relative to the multiple-cloning site (MCS) of the M13 vector.

EXAMPLE 3

A. Preparation of Single-Stranded Phage mOGO244 DNA and Site-Specific Mutagenesis to Construct Phage mOGO245

A 10 mL culture of early logarithmic growth phase *E. coli* K12 JM109 was inoculated with ~200 µl of phage stock (prepared in Example 2D) and incubated ~18 hours at 37° C. with aeration. The culture was centrifuged and the resulting supernatant transferred to a new tube and recentrifuged. The supernatant was again decanted to a fresh tube. One mL of a solution of 25% polyethylene glycol (molecular weight≈3,350) in 3 M NaCl was added to the supernatant, which was then incubated for 15 minutes at room temperature. The resulting mixture was centrifuged for 30 minutes at 10,000 rpm in a JA-14 rotor (Beckman). The pellet obtained by the centrifugation contained the single-stranded phage mOGO244 and was resuspended in 400 µl of TE buffer. The solution was extracted first with CHCl₃ and then with TE-saturated phenol. The phenol was allowed to stay in contact with the aqueous phase for 15 minutes. The solution was then extracted twice with a mixture of TE-saturated phenol:CHCl₃ (1:1, v/v), and twice with CHCl₃ alone. The DNA was then precipitated out of 0.3 M NaOAc. The DNA was collected by centrifugation, and the pellet was resuspended in 100 µl of 0.1 × TE buffer. This solution constituted ~5 µg of single-stranded phage mOGO244 DNA.

B. Mutagenesis

The single-stranded DNA fragments used in the mutagenesis (and subsequent hybridizations to detect desired phages) were synthesized on an automated DNA synthesizer, with the exception of the M13 universal primer (a 15-mer), which was purchased from BRL. The mutagenesis fragments were designated as follows: (1) SIPS6, a single-stranded DNA 36 nucleotides in length that is homologous to the IPNS coding sequence in phage mOGO244 except for three bases, the mismatch (underlined) of which will create a restriction enzyme NdeI recognition sequence at about position 1 of the IPNS coding sequence, with the DNA sequence:

NdeI
5'-CACACTCCACGGAGGATCATATGCCTGTCCTGATGC-3'; and (2) SIPS7, a single-stranded DNA 18 nucleotides in length that is merely a subfragment of SIPS6, with the DNA sequence:

NdeI
5'-GAGGATCATATGCCTGTC-3'.

The 5' ends of about 100 pmols of SIPS6 were phosphorylated (kinased) in a reaction mixture containing single-stranded DNA at a concentration of 1 pmol/µl, 10 µl of 10X ligase buffer, 1000 pmols adenosine triphosphate (ATP), 10 µl of 0.1 M DTT, 65 µl of glass-distilled water, and 1 µl (10 Richardson units) of T4 polynucleotide kinase (BMB). The reaction mixture was incubated at 37° C. for 30 minutes, at which time an additional 1 µl of enzyme was added. The reaction mixture was then incubated for another 30 minutes at 37° C. and then quenched by incubation at 68° C. for 5 minutes. The 5' ends of about 40 pmols of M13 universal primer were kinased in an analogous 40 µl of reaction mixture containing the same amount of enzyme.

The single-stranded phage mOGO244 DNA was mutagenized in substantial accordance with the teaching of Adelman et al., 1983, *DNA* 2(3): 183–193 as described below. The annealing reaction was carried out by adding ~500 nanograms (in 15 µl of 0.1X TE buffer) of single-stranded phage mOGO244 DNA to 8 µl of 10X annealing buffer (100 mM Tris-HCl, pH=7.5; 1 mM EDTA; and 500 mM NaCl), 4 µl (4 pmols) of kinased SIPS6, 4 µl (4 pmols) of kinased M13 universal sequencing primer, and 50 µl water, incubating the mixture at 80° C. for 2 minutes, then at 55° C. for 5 minutes, and finally at room temperature for 5 minutes.

The extension reaction was carried out by adding 120 μl of the following mixture to the solution of annealed DNA: 20 μl 10X Klenow-ligase buffer (100 mM Tris-HCl, pH =7.5; 1 mM EDTA; and 500 mM NaCl), 20 μl of 0.1 M DTT; 20 μl of a solution 6.25 mM in each of dGTP, dATP, TTP, and dCTP; 20 μl of 5 mM ATP; 120 μl of water 1 μl T4 DNA ligase (100–500 units, NEB), and 2.5 μl (12.5 units) of Klenow enzyme (BMB). The extension reaction mixture was incubated at room temperature for 1 hour, then at 37° C. for 4 hours, and finally at 14° C. for ~18 hours.

The extension reaction was extracted once with CHCl$_3$ and the DNA precipitated with ethanol and NaOAc and collected by centrifugation. The DNA pellet was resuspended in 400 μl 1× S1 buffer (0.3 M NaCl and 3 mM ZnOAc). Half the DNA solution was held in reserve at −20° C.; half was aliquoted to five 1.5 mL tubes. To four of these tubes was added 1 μl of S1 nuclease (BMB) that had been diluted to 200 30-minute units per μl. The reactions were incubated at room temperature for 5, 10, 15, and 20 minutes, respectively. The reactions were stopped by first adding 5–10 μg of tRNA to the reaction mixture to serve as carrier, then extracting with a TE-saturated phenol-CHCl$_3$ mixture (1:1, v/v). The sample that was not treated with S1 (the negative control) was also extracted. The DNA in the aqueous phase was concentrated by ethanol precipitation and collected by centrifugation. The DNA pellets were each resuspended in 20 μl water.

Ten μl of each of the resulting S1-treated DNA solutions were used to transform E. coli K12 JM109 in substantial accordance with the procedure described in Example 2D, except that the plates did not contain either X-Gal or IPTG. Desired mutants were identified by hybridization of radiolabelled oligonucleotide SIPS7 with phage DNA blotted onto nitrocellulose filters as described below.

After plaque formation, the plates were incubated at 4° C. for ~1 hour to harden the top agar. Nitrocellulose filters were placed on top of the lawn of each of two plates, containing ~50–200 plaques, from each of the negative control, the 10 minute S1, and the 20 minute S1-treated series. Contact between the filter and the surface of the lawn was maintained for ~1 minute, at which time the nitrocellulose filter was treated, by using saturated 3 MMChr filter papers (Whatman Lab-Sales, Inc., P.O. Box 1359, Hillsboro, Oreg. 97123-1359), with 0.1 N NaOH-1.5 M NaCl for ~5 minutes then 0.5 M Tris-HCl(pH=7.0)-3 M NaCl for ~5 minutes. The nitrocellulose filters were air-dried and then baked in vacuo at 80° C. for 30 minutes.

The nitrocellulose filters were prehybridized for ~5 minutes at room temperature in a solution of 6X SSC (20X SSC is 3 M NaCl and 0.3 M Na citrate), 10X Denhardt's solution (0.2 g of poly(vinylpyrollidone), 0.2 g of bovine serum albumin, and 0.2 g of Ficoll per 100 mL of water), 0.1% NaPPi, 0.1% SDS, and 10 μg/mL of denatured E. coli chromosomal DNA. The filters were then hybridized in a solution of 6X SSC, 10X Denhardt's solution, 0.1% NaPPi, and 1 pmol/5 mL of $^{32}$P-SIPS7. The $^{32}$P-SIPS7 was prepared by phosphorylating the 5' ends of 100 pmols of SIPS7 in substantial accordance with the procedure described earlier in this example, except that ~70 pmol of γ-$^{32}$P-ATP (New England Nuclear (NEN), 549 Albany Street, Boston, MA, 02118, Catalog #NEG-002A) were used instead of non-radioactive ATP. After hybridization, the filters were rinsed twice for 5 minutes per wash in excess 6X SSC at room temperature, then at 56° C. in excess 6X SSC for 20 minutes per wash. The filters were air-dried and autoradiographed for 2 hours at −70° C. with a Quanta III intensifying screen (DuPont). Desired mutants, those containing sequences complementary to the sequence of SIPS7, exposed the film due to binding of the radiolabelled oligomer by the phage DNA bound to the filter. The identity of a correct mutant, designated phage mOGO245, was confirmed by restriction analysis of its RF DNA, which was prepared in substantial accordance with the procedure described in Example 2D.

EXAMPLE 4

Construction of Plasmid pOGO246

Although the RF of phage mOGO245 contains the IPNS coding sequence on the NdeI-BamHI (partial) restriction fragment utilized in the construction of the E. coli expression plasmid pOGO249, it is sometimes difficult to accumulate the RF of mOGO245 in sufficient quantity for fragment isolation. To facilitate the construction of the E. coli expression plasmid pOGO249, the intermediate plasmid pOGO246 was constructed.

A. Restriction Enzyme SalI Digestion of Phage mOGO245 DNA

Replicative form DNA from phage mOGO245-infected E. coli K12 JM109 was isolated in substantial accordance with the procedure described in Example 2D. About 2 μg of the RF of phage mOGO245 DNA were digested with restriction enzyme SalI (~10 units) in a reaction containing the DNA in 1× SalI buffer. After incubation for ~90 minutes at 37° C., the reaction mixture was extracted with CHCl$_3$ and the DNA concentrated by precipitation with ethanol and NaOAc. The DNA was collected by centrifugation and the pellet resuspended in 10 μl of water.

B. Preparation of SalI-Digested Plasmid pUC19

SalI-digested plasmid pUC19 DNA (available from NEB) was prepared in substantial accordance with the procedure described in Example 2B.

Construction of Plasmid pOGO246

Five μl (~1 μg) of SalI-digested phage mOGO245 DNA and 1 μl (~100 ng) of SalI-digested plasmid pUC19 DNA were ligated in substantial accordance with the procedure described in Example 2C. The ligated DNA constituted the desired plasmid pOGO246 along with other ligation products. A restriction site and function map of plasmid pOGO246 is presented in FIG. 3 of the accompanying drawings.

D. Construction of E. coli K12 JM109/pOGO246

The ligation reaction constituting the desired plasmid pOGO246 was transformed into competent E. coli K12 JM109 (Stratagene) in substantial accordance with the manufacturer's protocol except that 1 mL of L broth was used for dilution. Aliquots of the transformation mixture were plated on L-agar plates containing ampicillin (100 μg/mL), X-gal (40 μg/mL), and IPTG (0.1 M). Plates were incubated at 37° C. for ~18 hours. Desired transformants were identified by their ampicillin-resistant phenotype and white colony color, due to insertional inactivation of β-galactosidase, and by restriction enzyme analysis of their plasmid DNA. Plasmid DNA was prepared from 3 mL cultures in substantial accordance with the procedure described in Example 2D for preparing RF DNA from phage M13-infected *E. coli* K12 JM109 cell pellets. Plasmid DNA from one transformant was prepared in substantial accordance with the procedure described in Example 1 for use in subsequent constructions.

EXAMPLE 5

Construction of Plasmid pOGO249

Plasmid pOGO249 was constructed by ligating together the following three DNA restriction fragments: an ~1.2 kb NdeI-BamHI restriction fragment from plasmid pOGO246 that contains the *Streptomyces lipmanii* IPNS coding sequence; an ~5.3 kb EcoRI-BamHI restriction fragment from plasmid pIT511 DNA that contains the DNA sequences coding for the cI857 repressor, the plasmid origin of replication, and the tetracycline resistance-conferring gene; and an ~520 bp EcoRI-NdeI restriction fragment from plasmid pBW33 DNA that contains the DNA sequences coding for the pL promoter and the translation activating sequence. Plasmid pIT511 is disclosed and claimed in U.S. patent application Ser. No. 021,836, filed Mar. 4, 1987. Plasmid pBW33 is disclosed and claimed in U.S. patent application Ser. No. 769,298, filed Aug. 26, 1985. One skilled in the art will recognize that different plasmids can share common DNA sequences encoding promoters, translation activating sequences, essential plasmid functions such as origin of replication, and plasmid features such as genes conferring antibiotic resistance. It is often matters of convenience rather than design that dictate choices for sources of DNA sequences, such as which plasmids are prepared and ready for use.

For ease of description, construction of plasmid pOGO249 will be taught using plasmid pCZR111 DNA as the source plasmid for the DNA sequences encoding the λpL promoter, the plasmid origin of replication, the cI857 gene, and the tetracycline resistance-conferring gene, and synthetic DNA as the source of the DNA encoding the transcription activating sequence.

A. Culture of *E. coli* K12 RV308/pCZR111 and Isolation of Plasmid pCZR111

A lyophil of *E. coli* K12 RV308/pCZR111 is obtained from the NRRL under the accession number NRRL B-18249. The lyophil is reconstituted in L broth; the resulting culture is used to prepare plasmid pCZR111 DNA in substantial accordance with the procedure described in Example 1. However, because the selectable marker on plasmid pCZR111 is the tetracycline resistance-conferring gene, the culture medium contains 10 μg/mL of tetracycline and no ampicillin. In addition, the culture is incubated at 25°-30° C., instead of 37° C., to prevent transcription from the lambda pL promoter. About 1 mg of plasmid pCZR111 DNA is obtained by this procedure and dissolved in ~1 mL of 0.1X TE buffer. A restriction site and function map of plasmid pCZR111 is presented in FIG. 4 of the accompanying drawings.

B. Isolation of the ~5.8 kb XbaI-BamHI Restriction Frgament of Plasmid pCZR111

Approximately 25 μg (in 25 μl of 0.1X TE buffer) of the plasmid pCZR111 DNA prepared in Example 5A are added to and mixed with 40 μl of 10× XbaI buffer (500 mM Tris-HCl, pH=8.0; 500 mM NaCl; and 100 mM MgCl$_2$), 335 μl of water, 2 μl (50 units) of restriction enzyme BamHI, and 3 μl (60 units) of restriction enzyme XbaI. The resulting reaction is incubated at 37° C. for 90 minutes. The DNA is concentrated by precipitation with ethanol and NaOAc and collected by centrifugation. The DNA pellet is resuspended in ~80 μl of water and ~20 μl of 5X loading buffer (70% glycerol, 50 mM EDTA, and 1 mg/mL bromphenol blue) and electrophoresed on an ~1.0% agarose gel until the desired ~5.8 kb XbaI-BamHI restriction fragment is clearly separated from the other digestion product, an ~600 bp XbaI-BamHI restriction fragment. Visualization of the electrophoresed DNA is accomplished by staining the gel in a dilute solution of ethidium bromide (~1 μg/μl) and exposing the gel to long-wave UV light.

The desired fragment is located, excised from the gel, and the ~5.8 kb XbaI-BamHI restriction fragment recovered using a D-Gel ™ DNA electroeluter (Epigene, Box 4817, Baltimore, MD, 21211) in substantial accordance with the manufacturer's directions. Two volumes of ethanol are added to the DNA, which is recovered from the eluter in 500 μl of 1 M NaCl. The resulting solution is incubated at −20° C. for ~5 hours, then centrifuged at 15,000 rpm for 20 minutes. The DNA pellet is rinsed first with 70% ethanol and then with 100% ethanol, dried, and resuspended in 20 μl of 0.1X TE buffer. This solution constitutes about 2 μg of the desired ~5.8 kb XbaI-BamHI restriction fragment and is stored at −20° C.

Isolation of the ~1.2 kb NdeI-BamHI Restriction Fragment of Plasmid pOGO246 DNA About 20 μg of plasmid pOGO246, as prepared in Example 4D, were digested to completion with restriction enzyme NdeI in a reaction containing 40 μl of 10X SalI buffer, plasmid pOGO246 DNA in 20 μl of 0.1X TE buffer, 340 μl of water, and 10 μl (~80 units) of restriction enzyme NdeI. The reaction was incubated at 37° C. for 90 minutes, and the digestion checked for completion by confirming the appearance of two restriction fragments, an ~1.9 kb fragment and an ~3.6 kb fragment, on a ~1.0% agarose analytical gel. The reaction mixture was extracted with CHCl$_3$, concentrated by precipitation with ethanol and NaOAc, and collected by centrifugation.

The DNA pellet was resuspended in 400 μl of 1X SalI buffer. About 2 μl (46 units) of restriction enzyme BamHI were added to the reaction mixture, which was then incubated at 37° C. for 5 minutes. The reaction was stopped by extraction with CHCl$_3$ and the DNA concentrated by precipitation with ethanol and NaOAc. The reaction progress was evaluated by running an aliquot of the digest on a 1% analytical agarose gel and looking for a complete range of the possible restriction fragments that could be generated by cutting at one, two, or three of the BamHI recognition sites present on the plasmid pOGO246 DNA at random. The DNA was then electrophoresed on a 1% agarose preparative gel until the desired ~1.2 kb NdeI-BamHI restriction fragment was separated from the other restriction fragments generated, which included ~0.20, ~0.47, ~0.58, ~0.65, and ~3.5 kb restriction fragments generated by complete digestion by restriction enzyme BamHI, and ~0.67, ~1.1, ~1.3, ~1.7, and ~1.9 kb restriction fragments generated by incomplete digestion by restriction enzyme BamHI. The desired ~1.2 kb NdeI-BamHI restriction fragment was recovered as described in Example 5B. The DNA pellet was resuspended in 10 μl water and constituted ~1 μg of the desired ~1.2 kb NdeI-BamHI restriction fragment.

D. Construction of an XbaI-NdeI Linker

Two complementary single-stranded DNA fragments can be synthesized on an automated DNA synthesizer and subsequently annealed to form a double-stranded fragment. Many DNA synthesizing instruments are known in the art and are suitable for making the fragments. One such instrument is an ABS 380A DNA Synthesizer (Applied Biosystems, Inc.). In addition, the fragment can also be conventionally prepared in substantial accordance with the procedures of Itakura et al., 1977, Science, 198:1056 and Crea et al., 1978, Proc. Natl. Acad. Sci. USA, 75:5765.

The following linkers are synthesized:

5'-CTAGAGGGTATTAATAATGTATCGCGATTTAAATAAGGAGGAATAACA-3' ; and

5'-TATGTTATTCCTCCTTATTTAAATCGCGATACATTATTAATACCCT-3'

About 100 pmols of each single-stranded DNA fragment are kinased in separate 50 μl reactions containing the single-stranded DNA fragment, 5 μl of 10X ligase buffer, 5 μl of 5 mM ATP, water to adjust the final reaction volume to 50 μl, and 1 μl (~10 Richardson units) of T4 polynucleotide kinase. The reactions are incubated at 37° C. for 30 minutes. The two reactions are then combined, and the resulting 100 μl of reaction mixture are heated to 90° C. and allowed to cool slowly to 4° C. to optimize annealing of the complementary single-stranded fragments. The resulting double-stranded DNA fragment is:

E. Final Construction of Plasmid pOGO249 and E. coli K12 JM109/pOGO249

One μl (0.1 μg) of the ~5.8 kb XbaI-BamHI restriction fragment of plasmid pCZR111, 1 μl of the ~1.2 kb NdeI-BamHI restriction fragment of plasmid pOGO246, and 1 μl of the synthetic XbaI-NdeI DNA fragment are ligated in substantial accordance with the procedure described in Example 2C. The ligated DNA constitutes the desired plasmid pOGO249. A restriction site and function map of plasmid pOGO249 is presented in FIG. 4 of the accompanying drawings. The ligation reaction was transformed into competent E. coli K12 JM109 cells (Stratagene) in substantial accordance with the manufacturer's directions. The transformation mixture was plated onto L-agar plates containing tetracycline (10 μg/mL) and the plates incubated at 25°–30° C. to prevent transcription from the lambda pL promoter. Desired transformants were identified by their tetracycline-resistant phenotype and restriction enzyme analysis of their plasmid DNA, which was prepared as described in Example 4D.

EXAMPLE 6

Assay of E. coli-Produced Isopenicillin N Synthetase

A Culture of E. coli K12 JM109/pOGO249 for Expression of Isopenicillin N Synthetase Activity An isolate of E. coli K12 JM109/pOGO249 was inoculated into ~5 mL of L broth containing 10 μg/ml tetracycline, and the culture was incubated in an air-shaker incubator at 30° C. for ~18 hours. One and one half mL of this culture were used to inoculate 15 mL of L broth containing 10 μg/mL tetracycline, and the resulting culture was incubated at 42° C. for 6 hours.

After the six-hour, 42° C. incubation, the culture was centrifuged and the cell pellet resuspended in ~1 mL of IPNS extraction buffer (0.05 M Tris-HCl, pH=8.0; 0.01 M KCl; and 0.1% Triton X-100). The cells were sonicated by six, ten-second bursts of sonication delivered by a Sonifier Cell Disruptor, Model W-225 (Heat Systems-Ultrasonics, Inc., Plainview, Long Island, NY) using the micro tip. The time between bursts of sonication was 30 seconds, and the mixture was kept in an ice bath during the procedure. After sonication, the cell mixture was centrifuged to remove debris and then used directly in the assay.

B. Assay for Isopenicillin N Synthetase Activity

The following assay procedure is derived from the procedure of Shen et al., 1984, J. of Antibiotics 37(9):1044–1048. The isopenicillin N synthetase assay reaction was carried out in a total volume of 500 μl. To start, 1 mL of a solution of 1.4 mM δ-(L-α-aminoadipyl)-L-cysteinyl-D-valine and 3.75 mM DTT was allowed to react at room temperature for 30 minutes to reduce any dimeric tripeptide to the monomeric form. Meanwhile, varying amounts of the cell extract, diluted with water to a volume of 350 μl, were dispensed into 1.5 mL tubes. Fifty μl of the following solution was aliquoted into each tube: 500 mM Tris-HCl, pH 7.4; 100 mM KCl; 100 mM MgSO₄; 2.0 mM FeSO₄; and 6.7 mM ascorbic acid. Finally, 100 μl aliquots of the tripeptide solution were added to each tube; this addition starts the reaction. Each tube was vortexed upon the addition of the substrate and incubated with gentle shaking at room temperature for 30 to 45 minutes.

After incubation, 2 samples of 150 μl each were withdrawn and dispensed into wells in the bioassay plates, and 100 units of penicillinase A were added to the remainder of the sample. The penicillinase A is obtained from Riker's Laboratories, Inc.; the enzyme is sold in vials of 100,000 units, which are rehydrated to 5.0 mL with H₂O. Five μl (100 units) of the rehydrated pencillinase A were added to the remainder of each reaction mixture, allowed to react for 5 minutes at room temperature, and then 100 μl of each penicillinase A-treated extract was dispensed into the wells of a bioassay plate.

This penicillinase A treatment is done to check that the zones on the bioassay plate are due to the presence of a penicillin rather than a cephalosporin or other contaminant.

The bioassay plates were composed of K131 nutrient agar, which is prepared by dissolving 30.5 g BBL Antibiotic Medium #11 (Becton Dickinson & Company, Cockeysville, MD) in 1 liter of deionized water, bringing the solution to a boil, cooling to 70° C., and then autoclaving 35 minutes at 121° C. and 15 psi. The plates were seeded with 4 ml of a fresh overnight culture of *Micrococcus luteus* (ATCC 9341) per 700 ml of agar. The *M. luteus* was grown in K544 nutrient broth, which is composed of: Difco peptone, 5.0 g; Difco yeast extract, 1.5 g; sodium chloride, 3.5 g; dipotassium phosphate (anhydrous), 3.7 g; monopotassium phosphate, 1.3 g; Difco beef extract, 1.5 g, in 1 liter of deionized water—the solution is brought to a boil, cooled to 25° C., adjusted to a pH=7.0 with 1 N HCl or 1 N NaOH, and then autoclaved for 20 minutes at 121° C. and 15 psi before use. The seeded agar was dispensed into 100×15 mm plates, at 15 mL of seeded agar per plate. The wells were prepared by applying suction using a disposable 5 ml pipette; each well was 10 mm in diameter.

After the plates were prepared and the samples dispensed into the wells, the plates were placed in a 37° C. incubator for 18 hours. The assay results were determined by measuring the diameter of the cleared areas around each sample well, which result from the *Micrococcus luteus* being unable to grow when a penicillin is present.

The results of the assay demonstrate that the *E. coli* K12 RV308/pOGO249 transformants express isopenicillin N synthetase activity.

We claim:

1. An isolated DNA compound that comprises a DNA sequence that encodes isopenicillin N synthetase originated from *Streptomyces lipmanii*.

2. The isolated DNA compound of claim 1 that comprises DNA that encodes the amino acid residue sequence:

H₂N-Met Pro Val Leu Met Pro Ser Ala Asp Val Pro Thr Ile Asp

Ile Ser Pro Leu Phe Gly Thr Asp Pro Asp Ala Lys Ala His Val

Ala Arg Gln Ile Asn Glu Ala Cys Arg Gly Ser Gly Phe Phe Tyr

-continued

Ala Ser His His Gly Ile Asp Val Arg Arg Leu Gln Asp Val Val

Asn Glu Phe His Arg Thr Met Thr Asp Gln Glu Lys His Asp Leu

Ala Ile His Ala Tyr Asn Glu Asn Asn Ser His Val Arg Asn Gly

Tyr Tyr Met Ala Arg Pro Gly Arg Lys Thr Val Glu Ser Trp Cys

Tyr Leu Asn Pro Ser Phe Gly Glu Asp His Pro Met Ile Lys Ala

Gly Thr Pro Met His Glu Val Asn Val Trp Pro Asp Glu Glu Arg

His Pro Asp Phe Arg Ser Phe Gly Glu Gln Tyr Tyr Arg Glu Val

Phe Arg Leu Ser Lys Val Leu Leu Leu Arg Gly Phe Ala Leu Ala

Leu Gly Lys Pro Glu Glu Phe Phe Glu Asn Glu Val Thr Glu Glu

Asp Thr Leu Ser Cys Arg Ser Leu Met Ile Arg Tyr Pro Tyr Leu

Asp Pro Tyr Pro Glu Ala Ala Ile Lys Thr Gly Pro Asp Gly Thr

Arg Leu Ser Phe Glu Asp His Leu Asp Val Ser Met Ile Thr Val

Leu Phe Gln Thr Glu Val Gln Asn Leu Gln Val Glu Thr Val Asp

Gly Trp Gln Ser Leu Pro Thr Ser Gly Glu Asn Phe Leu Ile Asn

Cys Gly Thr Tyr Leu Gly Tyr Leu Thr Asn Asp Tyr Phe Pro Ala

Pro Asn His Arg Val Lys Tyr Val Asn Ala Glu Arg Leu Ser Leu

Pro Phe Phe Leu His Ala Gly Gln Asn Ser Val Met Lys Pro Phe

His Pro Glu Asp Thr Gly Asp Arg Lys Leu Asn Pro Ala Val Thr

Tyr Gly Glu Tyr Leu Gln Glu Gly Phe His Ala Leu Ile Ala Lys

Asn Val Gln Thr —COOH wherein ALA is an Alanine residue, ARG is an Arginine residue, ASN is an Asparagine residue, ASP is an Aspartic Acid residue, —COOH is the carboxy-terminus, CYS is a Cysteine residue, GLN is a Glutamine residue, GLU is a Glutamic Acid residue, GLY is a Glycine residue, HIS is a Histidine residue, H₂N— is the amino terminus, ILE is an Isoleucine residue, LEU is a Leucine residue, LYS is a Lysine residue, MET is a Methionine residue, PHE is a Phenylalanine residue, PRO is a Proline residue, SER is a Serine residue, THR is a Threonine residue, TRP is a Tryptophan residue, TYR is a Tyrosine residue, and VAL is a Valine residue.

3. The isolated DNA compound of claim 2 that comprises the DNA sequence:

5'-ATGCCTGTCCTGATGCCGTCGGCCGACGTGGCCGACATCGACATCTCCCCCCTGTTCGGG

ACCGACCCGGACGCCAAGGCGCACGTCGCGCGGCAGATCAACGAGGCCTGCCGCGGTTCG

GGCTTCTTCTACGCCTCCCACCACGGCATCGACGTGCGGCGGCTGCAGGACGTGGTCAAC

GAGTTCCACCGGACCATGACCGACCAGGAGAAGCACGACCTGGCGATCCACGCGTACAAC

GAGAACAACTCGCATGTGCGCAACGGTTATTACATGGCCCGCCCGGGCCGGAAGACCGTC

GAGTCCTGGTGCTACCTGAACCCGTCGTTCGGCGAGGACCACCCGATGATCAAGGCCGGG

ACGCCGATGCACGAGGTGAACGTCTGGCCGGACGAGGAACGCCATCCGGACTTCCGGTCC

TTCGGCGAGCAGTACTACCGCGAGGTGTTCCGGCTCTCGAAGGTGCTGCTGCTGCGGGGC

TTCGCGCTGGCGCTCGGCAAGCCGGAGGAGTTCTTCGAGAACGAGGTCACCGAGGAGGAC

ACCCTCTCCTGCCGATCTCTGATGATCCGGTACCCGTACCTGGATCCGTACCCGGAAGCG

GCGATCAAGACGGGCCCGGACGGCACCAGGCTCAGCTTCGAGGACCACCTCGACGTGTCG

-continued
ATGATCACCGTCCTGTTCCAGACCGAGGTGCAGAACCTCCAGGTCGAGACGGTGGACGGG

TGGCAGAGCCTGCCGACGTCCGGGGAGAACTTCCTGATCAACTGCGGCACCTACCTGGGG

TACCTCACGAACGACTACTTCCCGGCCCCCAACCACCGGGTCAAGTACGTCAACGCGGAA

CGCCTGTCCCTGCCGTTCTTCCTCCACGCCGGGCAGAACAGCGTGATGAAGCCGTTCCAC

CCGGAGGACACCGGCGACCGGAAGCTCAACCCGGCCGTCACGTACGGGGAGTACCTGCAA

GAGGGCTTCCACGCGCTGATCGCGAAGAACGTCCAGACC-3' wherein A is deoxyadenyl, G is deoxyguanyl, C is deoxycytidyl, and T is thymidyl.

4. The isolated DNA compound of claim 1 selected from the group consisting of the ~2.8 kb SalI restriction fragment of plasmid pOGO239 and the ~1.2 kb NdeI-BamHI restriction fragment of plasmid pOGO246.

5. The isolated DNA compound of claim 1 that is a plasmid.

6. The plasmid of claim 5 that is plasmid pOGO239.
7. The plasmid of claim 5 that is plasmid pOGO246.
8. The plasmid of claim 5 that is plasmid pOGO246.

9. The isolated DNA compound of claim 1 that is a phage.

10. The phage of claim 9 selected from the group consisting of phages mOGO244 and mOGO245.

11. A recombinant DNA host cell transformed with a recombinant DNA vector that encodes isopenicillin N synthetase originated from *Streptomyces lipmanii*.

12. The host cell of claim 11 that is *E. coli*.
13. The host cell of claim 11 that is Streptomyces.
14. The host cell of claim 11 that is Penicillium.
15. The host cell of claim 11 that is Cephalosporium.
16. The isolated DNA compound of claim 1 that comprises the ~1.2 kb SalI-PstI restriction fragment of plasmid pOGO239.

17. The isolated DNA compound of claim 1 that comprises the ~1 kb SalI-NdeI restriction fragment of plasmid pOGO246.

18. The isolated DNA compound of claim 1 that comprises the DNA sequence:

5'-GCAAGACACCGCACGCCATGTCCAGCGCCCACGCCTGGCGCACACTCCACGGAGGATGCC-3' wherein A is deoxyadenyl, G is deoxyguanyl, C is deoxycytidyl, and T is thymidyl.

19. The isolated DNA compound of claim 1 that is the ~0.94 kb KpnI-SalI restriction fragment of plasmid pOGO239.

20. The isolated DNA compound of claim 19 that comprises the DNA sequence:

5'-TGAGCAATCGTCAAACTGTGAGCTGGTGAAGGAGCTTGCCGGGCACAGCGTGGTGCCCGGCGG-3' wherein A is deoxyadenyl, G is deoxyguanyl, C is deoxycytidyl, and T is thymidyl.

21. An isolated DNA compound that comprises the transcription and translation activating sequence of the isopenicillin N synthetase gene of *Streptomyces lipmanii*.

22. An isolated DNA compound that comprises a DNA sequence that encodes the transcription termination and polyadenylation signals of the isopenicillin N synthetase gene of *Streptomyces lipmanii*.

23. The host cell of claim 12 that is selected from the group consisting of *E. coli* K12 JM109/pOGO239, *E. coli* K12 JM109/pOGO246, and *E. coli* K12 JM109/pOGO249.

* * * * *

UNITED STATES PATENT AND TRADEMARK OFFICE
CERTIFICATE OF CORRECTION

PATENT NO. : 4,950,603

DATED : August 21, 1990

INVENTOR(S) : Ingolia et al.

It is certified that error appears in the above-identified patent and that said Letters Patent is hereby corrected as shown below:

Col. 29,
In Claim 8, change "pOGO246" to -- pOGO249 --.

In Claim 13, change "Streptomyces" to -- Streptomyces --.

In Claim 14, change "Penicillium" to -- Penicillium --.

In Claim 15, change "Cephalosporium" to -- Cephalosporium --.

Signed and Sealed this

Nineteenth Day of January, 1993

Attest:

DOUGLAS B. COMER

*Attesting Officer*  Acting Commissioner of Patents and Trademarks